United States Patent [19]

Zobrist et al.

[11] 4,283,957
[45] Aug. 18, 1981

[54] TORSIONAL EXCITER FOR A ROTATING STRUCTURE

[75] Inventors: Gerald S. Zobrist; Terry A. Dunlap, both of Cincinnati; Richard H. Russell, Milford, all of Ohio

[73] Assignee: Zonic Corporation, Cincinnati, Ohio

[21] Appl. No.: 51,947

[22] Filed: Jun. 25, 1979

[51] Int. Cl.³ ............................................. G01N 3/36
[52] U.S. Cl. ........................................ 73/814; 73/847
[58] Field of Search ................. 73/814, 847, 662, 665

[56] References Cited

U.S. PATENT DOCUMENTS

| | | | |
|---|---|---|---|
| 2,157,903 | 5/1939 | Lapsley | 73/814 |
| 2,384,987 | 9/1945 | Dudley | 73/662 |
| 2,452,031 | 10/1948 | Allnutt et al. | 73/650 |
| 3,112,643 | 12/1963 | Lanahan | 73/847 |
| 3,495,447 | 2/1970 | Conniff et al. | 73/814 |
| 3,693,402 | 9/1972 | Jones | 73/814 |
| 3,772,913 | 11/1973 | Zell et al. | 73/579 |
| 3,871,210 | 3/1975 | Himmler et al. | 73/570 |

*Primary Examiner*—Anthony V. Ciarlante
*Attorney, Agent, or Firm*—Wood, Herron & Evans

[57] ABSTRACT

An exciter is disclosed for applying a dynamic torsional force to a rotating structure, such as to the shaft of a turbine generator, the axle of a vehicle, or the like, during mechanical testing to determine the mechanical response characteristics, natural modes of vibration, fatigue life, etc., of the structure. The exciter includes a rotary hydraulic actuator having a housing secured to the structure to be tested and a driveshaft which is rotatable relative to the housing as well as an inertial mass mounted on the driveshaft. The exciter also includes a hydraulic power supply for the actuator and an electrohydraulic means comprising a torque setpoint circuit for producing a torque command signal to set the desired amplitude and frequency of oscillation of the inertial mass, a position setpoint circuit for producing a position command signal to set the midpoint of the arc through which the inertial mass oscillates, means for producing a torque feedback signal dependent on the actual dynamic torsional force produced by the oscillating inertial mass, means for producing a position feedback signal dependent on the average angular position of the inertial mass relative to the structure as the inertial mass oscillates and a controller responsive to the command and feedback signals for energizing a servovalve that controls the supply of pressurized fluid to the actuator. The actuator oscillates the inertial mass relative to the structure to be tested in order to produce a controlled dynamic torsional force on the rotating structure.

26 Claims, 6 Drawing Figures

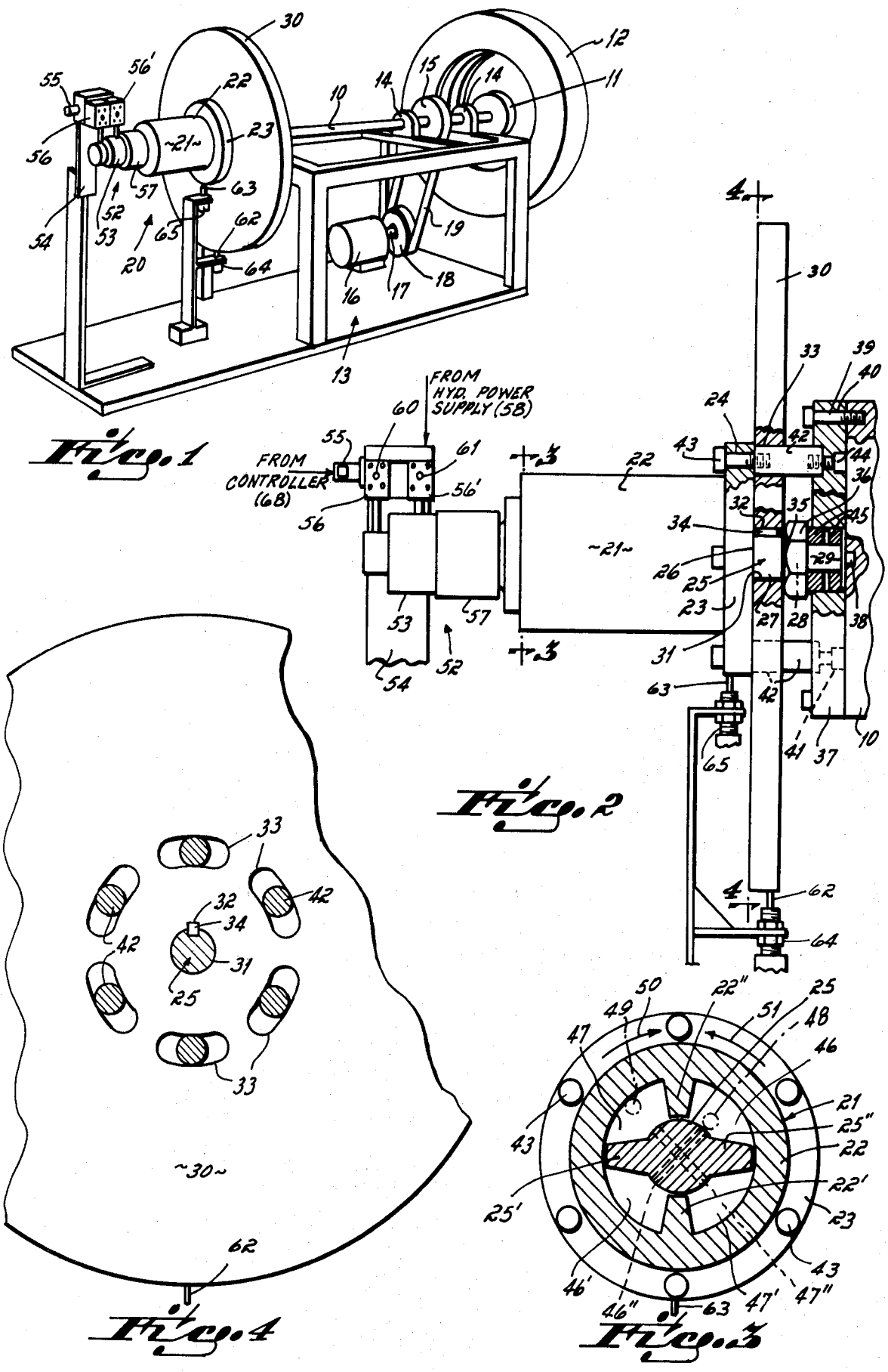

TORSIONAL EXCITER FOR A ROTATING STRUCTURE

BACKGROUND OF THE INVENTION

This invention relates to exciters for applying a force to a structure undergoing mechanical testing in order to study the mechanical response characteristics, modes of vibration or fatigue life of the structure. More particularly, the present invention is directed to an exciter for applying a dynamic torsional force to a rotating structure, such as to the shaft of an electrical generator or motor, the propeller shaft of a ship, or the like, during rotation.

Torsional exciters are known for testing a rotating structure under full speed and full load. One type of machine is shown in U.S. Pat. Nos. 2,157,903 and 3,112,643 and includes two lines of shafting geared together at opposite ends. The structure to be tested is interposed in one line of shafting. A motor or the like simultaneously drives the two lines of shafting. The lines of shafting are interconnected by means of a torque coupling which acts through one line of shafting and reacts against the other line of shafting so as to apply a torque to the structure to be tested. Such machines, however, have several disadvantages. The variety of structures which can be tested is limited by the physical dimensions of the lines of shafting, and, therefore, the machines do not have universal application. Furthermore, the torque couplings included in the machines are relatively complex and expensive to construct as well as difficult to adjust for applying a desired torque to the structure to be tested.

Another type of machine is disclosed by U.S. Pat. No. 2,384,987 and includes a circuit for energizing an electrical motor which rotates a structure to be tested wherein the circuit also superimposes an oscillatory signal for energizing the motor for producing a dynamic torsional force on the rotating structure. U.S. Pat. No. 3,495,447 discloses the use of two motors for mechanical testing, one energized for rotating a structure to be tested and the other connected in series with the first motor and the structure to be tested and energized for applying torque to the rotating structure. U.S. Pat. No. 3,693,402 discloses an electromagnetic exciter including a disc rotatable with a structure to be tested. The disc includes a plurality of radially extending members of magnetically permeable material. A magnetic field is generated through which the disc rotates. The field initially attracts the members to apply a positive torque and then tends to retain the members to apply a negative torque. Consequently, a vibrational torque is applied to the rotating structure. One disadvantage is that these machines are openloop. As a result, the torque applied to the rotating structure is not precisely controlled.

Another type of machine is disclosed by U.S. Pat. No. 2,452,031 and includes a motor for rotating a flywheel as well as a structure to be tested. The flywheel includes sector-shaped openings in which arms are mounted for pivotal movement. The arms are centered by means of compression springs within the sector-shaped openings. The arms are moved about the center position by a hydraulic device for producing a dynamic torsional force on the rotating structure. The frequency of torsional oscillation may be adjusted by varying the speed of a hydraulic pump motor, and the amplitude of torsional oscillation may be varied by adjusting the stroke of the pump. However, the machine is open-loop which is disadvantageous because the dynamic torsional force applied to the rotating structure cannot be controlled with a high degree of precision. Furthermore, adjustment of the speed of the hydraulic pump motor and the stroke of the pump for setting the desired frequency and amplitude of the dynamic torsional force is cumbersome. Moreover, conventional pump motors normally operate at 1800 RPM which translates into a maximum excitation frequency of 30 Hz. Consequently, the machine disclosed by U.S. Pat. No. 2,452,031 cannot be employed for mechanically testing turbine generators, for example, where 60 Hz., 120 Hz., 180 Hz. and other harmonic excitation frequencies are required.

One objective of the present invention is to provide an exciter for applying a dynamic torsional force to any size or shape of rotating structure.

Another objective is to provide a torsional exciter which includes many readily available off-the-shelf components, is easy to construct and is relatively inexpensive to manufacture.

An additional objective is to provide an exciter of the above type which can be easily adjusted for producing an dynamic torsional force having a desired amplitude and frequency.

Another objective is to provide an exciter of the above type with the capability for applying a dynamic torsional force having a frequency as high as 1000 Hz.

A further objective is to provide an exciter of the above type which is closed-loop so that the dynamic torsional force applied to the rotating structure can be precisely controlled.

SUMMARY OF THE INVENTION

The above and other objectives are achieved in accordance with a preferred embodiment of the present invention which provides an exciter for applying a dynamic torsional force to a rotating structure having any physical size or shape. The exciter includes a rotary hydraulic actuator mounted directly on the structure, such as to the shaft of a turbine generator, the axle of a vehicle, or the like.

The rotary hydraulic actuator preferably includes two elements. A first element, or housing, is secured to the structure to be tested. The second element, or driveshaft, is rotatable relative to the housing. An inertial mass is mounted on the driveshaft.

In the preferred embodiment, the inertial mass is a disc keyed to the driveshaft. The disc includes arcuate slots through which mounting means extends for securing the housing to the structure to be tested. The disc can rotate through an arc dependent on the length of the slots.

A hydraulic power supply is included for supplying pressurized fluid to the actuator. Preferably, the hydraulic power supply is connected to the actuator through manifolds and a rotating union.

An electrohydraulic means is included for controlling the supply of pressurized fluid to the actuator so that a desired dynamic torsional force is applied to the structure to be tested. In the preferred embodiment, a torque setpoint circuit is provided for selectively producing a torque command signal to set the desired amplitude and frequency of oscillation of the disc. The torque setpoint circuit preferably is adjustable to also effect random variation in the amplitude and/or frequency range of the torque applied to the rotating structure. Means is also included for producing a torque feedback signal dependent on the actual dynamic torsional force produced by the oscillating disc. Preferably, a position setpoint circuit is provided for selectively producing a position command signal to set the midpoint of the arc through which the disc oscillates. Also included is means for producing a position feedback signal dependent on the average angular position of the disc relative to the structure as the disc oscillates.

In the preferred embodiment, the means for producing the torque feedback signal includes pressure transducers for converting the pressures in the two chambers of the actuator into electrical signals correlated to pressure and an interface circuit responsive to the pressure signals for producing a differential pressure signal. The differential pressure signal is dependent on the amplitude and frequency of the actual dynamic torsional force applied to the rotating structure and comprises the torque feedback signal. The means for producing the position feedback signal preferably includes a first pin fixed to the housing of the actuator and a second pin fixed to the disc which are sensed by detectors for producing position signals and an interface circuit responsive to the position signals for producing an average position signal. The average position signals is dependent on the average angular position of the disc relative to the structure as the disc oscillates, that is, the angular position about which oscillation of the disc is symmetric. The average position signal comprises the position feedback signal.

Finally, a controller is provided for producing a control signal for energizing a servovalve for controlling the supply of pressurized fluid through the manifold to the actuator dependent on the command and feedback signals. The controller is closed-loop so as to exert precise control over the actuator so that the actuator oscillates the disc for applying a controlled dynamic torsional force to the rotating structure.

The present invention provides a universal torsional exciter for mechanically testing a rotating structure. The exciter is simple in design and easy to construct and, furthermore, includes many off-the-shelf components, such as the actuator, rotating union, hydraulic power supply and controller. As a result, the exciter is relatively inexpensive to manufacture. The inclusion of setpoint circuits facilitates adjustments for producing a desired dynamic torsional force on the rotating structure. Since the controller is closed-loop, control over the dynamic torsional force applied to the rotating structure is precise.

The above and other features and advantages of the present invention will be better understood by those of skill in the field to which the present invention appertains after a consideration of the following description in connection with the accompanying drawing in which:

FIG. 1 illustrates the torsional exciter of the present invention included in a mechanical testing apparatus;

FIG. 2 is a partly elevational and partly sectional view of the exciter shown in FIG. 1;

FIG. 3 is a cross-sectional view along the line 3—3 in FIG. 2;

FIG. 4 is a cross-sectional view along the line 4—4 in FIG. 2;

Figure 5:
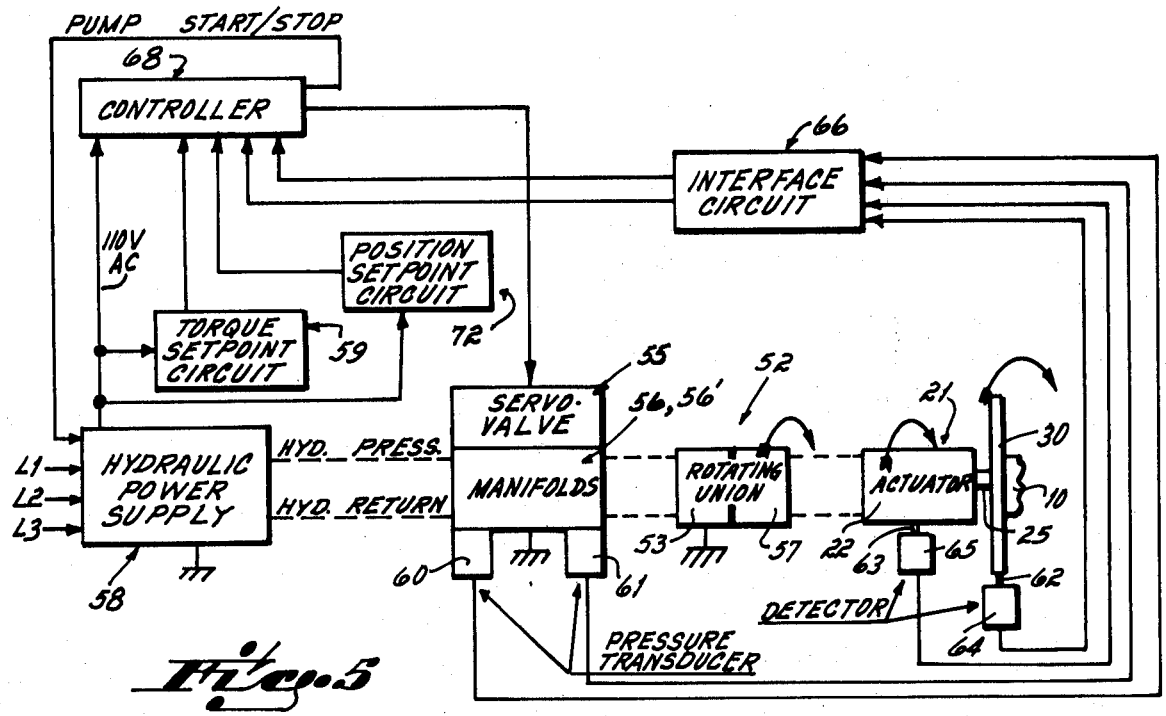
FIG. 5 is a block diagram which shows the electrohydraulic means of the exciter of the present invention.

The torsional exciter of the present invention is particularly useful for applying a dynamic torsional force to a rotating structure, such as to the shaft of a turbine generator, the axle of a vehicle, or the like, during mechanical testing to determine the mechanical response characteristics, natural modes of vibration, fatigue life, etc., of the structure. For example, a mechanical testing apparatus including the torsional exciter of the present invention is illustrated in FIG. 1.

As shown in FIG. 1, a vehicle axle undergoing mechanical testing is indicated by the numeral 10. A wheel 11 and a tire 12 are shown mounted on the axle. The axle 10 is rotatably supported on a test frame 13 in bearings 14 secured to the test frame.

The mechanical testing apparatus includes a drive for rotating the structure to be tested formed by the axle 10, wheel 11 and tire 12. As shown in FIG. 1, the drive preferably includes a motor 16 having a shaft 17 and a drivetrain comprising a first pulley 15 fixed to the axle 10, a second pulley 18 fixed to the shaft 17 and a belt 19 trained over the pulleys. The motor 16 is preferably electrical or hydraulic and may be a variable speed motor. The motor 16 is selectively energized for rotating the shaft 17 to drive the pulley 18. The belt 19 trained over the pulleys 15 and 18 in turn drives the pulley 15 so that the structure to be tested formed by the axle 10, wheel 11 and tire 12 is rotated at a predetermined speed. Of course, the pulleys 15 and 18 can be sized so that the structure to be tested rotates faster or slower or at the same angular velocity as the shaft 17.

Further operation of the mechanical testing apparatus in FIG. 1 will be described in detail later. A preferred embodiment for the torsional exciter of the present invention will first be presented.

The torsional exciter of the present invention is indicated generally by the numeral 20 in FIG. 1. As pointed out above, the torsional exciter of the present invention is for applying a dynamic torsional force to the structure to be tested during rotation.

The exciter includes a rotary drive 21 which is actually mounted on and rotates with the structure to be tested. The rotary drive is preferably a rotary hydraulic actuator, such as a double-vane high pressure Rotac ® actuator manufactured by Ex-Cell-O Corporation of Detroit, Michigan.

As shown in FIG. 2, the actuator 21 includes a housing 22 having an integral head 23. The head includes holes 24 which are provided for securing the actuator to the structure to be tested as will be described later.

The actuator 21 also includes a driveshaft 25. The driveshaft is coaxial with the housing 22 and is rotatably mounted relative to the housing. The driveshaft 25 preferably has a shoulder 26, a key-retaining section 27, a threaded section 28 and a bearing section 29.

As shown in FIGS. 1 and 2, an inertial mass, or disc, 30 is mounted on the driveshaft 25 of the actuator 21. The disc 30 is shown in detail in FIG. 4 and includes a central hole 31 having a keyway 32 and further includes several arcuate slots 33. The disc is mounted on the driveshaft 25 by aligning the keyway 32 with a key 34 fixed to the key-retaining section 27 of the driveshaft and by sliding the disc onto the driveshaft until the disc abuts the shoulder 26. The key 34 and keyway 32 are located so that the holes 24 in the head 23 are aligned with the arcuate slots 33 when the driveshaft 25 is rotated relative to the housing 22. A washer 35 is slid onto the driveshaft 25 and a locknut 36 is screwed onto the threaded section 28 of the driveshaft to lock the disc 30 on the driveshaft.

As shown in FIG. 2, a mounting plate 37 is preferably provided for securing the housing 22 of the actuator 21 to the structure to be tested. The mounting plate includes locating pins 38 for positioning the actuator. Bolts 39 extend through holes 40 in the mounting plate and screw into threaded holes provided in the structure to be tested.

The housing 22 of the actuator 21 is in turn secured to the mounting plate 37 as shown in FIG. 2. The mounting plate is provided with holes 41. Threaded spacers 42 pass through the arcuate slots 33 in the disc 30 and are aligned with the holes 24 in the head 23 of the housing 22 as well as with the holes 41 in the mounting plate 37. Bolts 43 extend through the holes 24 in the head 23 and screw into the threaded spacers 42. Bolts 44 extend through the holes 41 in the mounting plate 37 and also screw into the threaded spacers 42.

As shown in FIG. 2, the central portion of the mounting plate 37 is preferably relieved to receive bearings 45. The bearings 45 rotatably support the bearing section 29 of the driveshaft 25.

Referring to FIG. 3, the housing 22 of the actuator 21 includes internal vanes 22' and 22". The driveshaft 25 of the actuator includes vanes 25' and 25'. Consequently, the interior of the actuator 21 includes four regions 46, 46', 47 and 47'.

The regions 46 and 46' are interconnected by a duct 46" in the driveshaft 25, and the regions 47 and 47' are interconnected by a duct 47" in the driveshaft. The region 46, duct 46" and region 46' form a first chamber in hydraulic circuit with a port 48. Similarly, the region 47, duct 47" and region 47' form a second chamber in hydraulic circuit with a port 49.

The actuator 21 is conventional and operates on a differential pressure principle. That is, pressurized fluid is supplied to the port 48 and to the port 49. If the pressure is greater at the port 48, the driveshaft 25 will rotate clockwise relative to the housing 22. Since the disc 30 is fixed to the diveshaft, the disc will be driven clockwise as shown by the arrow 50 in FIG. 3. On the other hand, if the pressure is greater at the port 49, the driveshaft 25 will rotate counterclockwise relative to the housing 22, and the disc 30 will be driven counterclockwise as shown by the arrow 51 in FIG. 3.

As pointed out earlier, the actuator 21 and disc 30 are mounted on and rotate with the structure to be tested. As shown in FIGS. 1 and 2, a fluid coupling 52 is connected to the ports 48 and 49 of the actuator 21. The fluid coupling is preferably a rotating union, such as a Deuplex rotating union manufactured by the Deublin Company of Northbrook, Illinois. The stationary section 53 of the rotating union is interconnected to the ports 48 and 49 of the actuator 21 by the rotary section 57 of the rotating union. A servovalve 55 controls the supply of pressurized fluid from a hydraulic power supply 58 (FIG. 5) to the stationary section 53 of the rotating union through manifolds 56 and 56' mounted on a bracket 54 secured to the test frame 13.

The entire electrohydraulic means for controlling the supply of pressurized fluid to the actuator 21 is shown in FIG. 5. Hydraulic connections are indicated in FIG. 5 by dashed lines while electrical connections are indicated by solid lines.

The hydraulic power supply 58, manifolds 56, 56', rotating union 52, actuator 21 and disc 30 are connected in a hydraulic circuit as shown in FIG. 5. The hydraulic power supply 58, the manifolds 56, 56' and the stationary section 53 of the rotating union 52 are stationary. The rotary section 57 of the rotating union, the housing 22 as well as the driveshaft 25 of the actuator 21 and the disc 30 rotate with the structure to be tested as indicated by the arrows in FIG. 5. The servovalve 55 controls the supply of pressurized fluid to the actuator 21 for oscillating the disc 30 in order to produce a controlled dynamic torsional force on the structure to be tested.

As shown in FIG. 5, the hydraulic power supply 58 is connected to a source of electrical power L1–L3 for energizing a pump motor included in the hydraulic power supply. The hydraulic power supply is preferably an Xcite 1100 Series Hydraulic Power Supply manufactured by Zonic Technical Laboratories, Inc. of Cincinnati, Ohio.

A torque setpoint circuit 59 included in the electrohydraulic means is adjusted for providing a preselected torque command signal to set the desired amplitude and frequency of the dynamic torsional force applied to the rotating structure. The torque command signal is preferably a sinusoidal signal having a preselected amplitude and frequency. The maximum excitation frequency is preferably at least 1000 Hz. The torque setpoint circuit may produce a periodic signal having a different waveform, such as a triangular waveform rather than a sinusoidal waveform, or may even produce a torque command signal having a random frequency and/or amplitude if desired. A position setpoint circuit 72 preferably included in the electrohydraulic means is adjusted for providing a position command signal to set the midpoint of the arc through which the disc oscillates.

The electrohydraulic means also includes means for producing feedback signals dependent on the actual dynamic torsional force produced by the oscillating disc as well as the average angular position of the disc relative to the structure as the disc oscillates. A means for producing a torque feedback signal will be described first.

The torque on the rotating structure is preferably determined from the pressures in the respective chambers 46, 46', 46" and 47, 47', 47" of the actuator 21 by producing a signal representing the differential pressure between the chambers. The differential pressure signal is dependent on the actual dynamic torsional force applied to the rotating structure. Compare, for example, U.S. Pat. No. 3,772,913.

As described above in conjunction with FIG. 2, pressurized fluid is introduced into the respective chambers 46, 46', 46" and 47, 47', 47" of the actuator 21 through the manifolds 56, 56'. The pressures in the manifolds 56, 56', therefore, equal the pressures in the respective chambers 46, 46', 46" and 47, 47', 47". Since the actuator 21 is mounted on and rotates with the structure to be tested and the manifolds 56, 56' are stationary, the pressures are preferably transduced in the manifolds so that slip rings or like electrical contacts are not needed.

As shown in FIGS. 2 and 5, a first pressure transducer 60 is mounted on the manifold 56 for transducing the pressure in the chamber 46, 46', 46", of the actuator 21 while a second pressure transducer 61 is mounted on the manifold 56' for transducing the pressure in the chamber 47, 47', 47" of the actuator. The pressure transducers 60 and 61 produce pressure signals dependent on the pressures in the respective chambers 46, 46', 46" and 47, 47', 47" of the actuator.

As indicated above, the electrohydraulic means also preferably includes means for producing a position feedback signal dependent on the average angular position of the disc 30 relative to the structure as the disc oscillates. As described in conjunction with FIG. 2, the housing 22 of the actuator 21 is secured to structure to be tested while the disc 30 is mounted on the driveshaft 24 of the actuator. Since the housing 22 is secured to structure to be tested, the angular position of the disc relative to the structure is conveniently determined based on the angular position of the disc 30 relative to the housing.

As shown in FIG. 2, a first pin 62 of magnetically permeable material is fixed to the disc 30, and a second pin 63 of magnetically permeable material is fixed to the head 23 of the housing 22. A first magnetic detector 64 is located near the disc 30 for sensing whenever the pin 62 rotates by. A second magnetic detector 65 is disposed in the vicinity of the head 23 for sensing whenever the pin 63 rotates by. Preferably, the pin 62 is fixed to the perimeter of the disc 30 and the pin 63 is fixed to the head 23 so that the pins are simultaneously sensed by the detectors 64 and 65 when the spacers 42 are at one end of the slots 33 of the disc 30 as will be explained more fully later.

As shown in FIG. 5, the pressure transducers 60 and 61 and the detectors 64 and 65 are connected to an interface circuit 66. The interface circuit is responsive to the pressure transducer signals for producing a torque feedback signal dependent on the actual dynamic torsional force applied to the rotating structure. The interface circuit is also responsive to the detector signals for producing a position feedback signal dependent on the average angular position of the oscillating disc 30 relative to the structure for a purpose which will be explained later.

Figure 6:
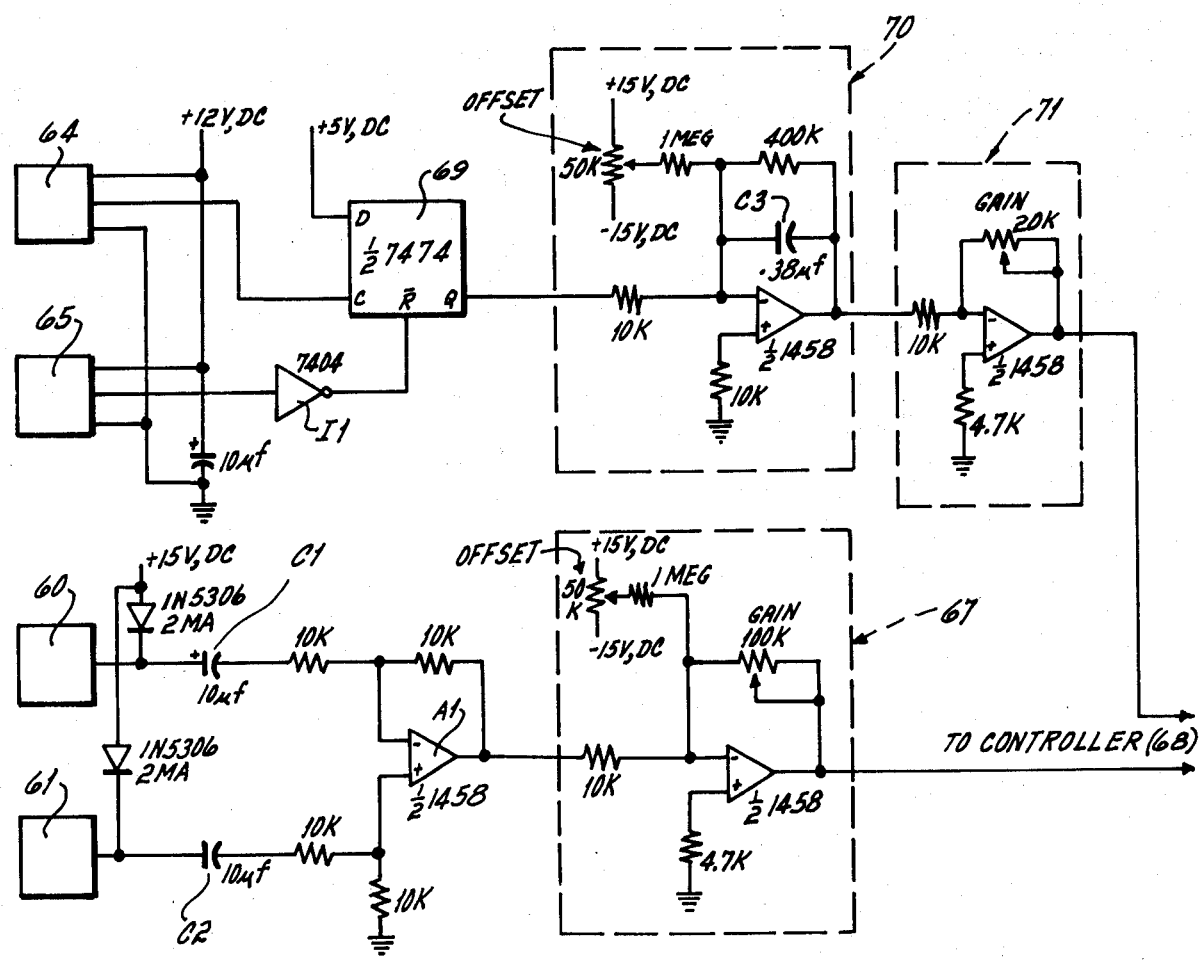
FIG. 6 is a schematic diagram of the interface circuit in FIG. 5.

The interface circuit 66 is shown in more detail in FIG. 6. The signal from the pressure transducer 60 is input through a coupling capacitor C1 to one input of a differential amplifier A1. The signal from the pressure transducer 61 is input through a coupling capacitor C2 to the other input of the differential amplifier A1. The differential amplifier A1 produces a signal dependent on the difference in pressure between the chambers 46, 46', 46" and 47, 47', 47" of the actuator 21. The output of the differential amplifier A1 is connected to a signal level shifting and amplifying circuit 67 which produces a torque feedback signal comprising one input to a controller 68 as shown in FIG. 5.

As indicated above, the interface circuit 66 is also responsive to the detector signals for producing a position feedback signal dependent on the average angular position of the oscillating disc 30 relative to the structure. As shown in FIG. 6, the detector 64 is connected to the clock input of a continuously enabled D flip-flop 69. As the disc 30 rotates with the structure to be tested, the signal produced by the detector 64 will comprise a series of pulses, one pulse each time that the pin 62 rotates by the detector 64.

The signal produced by the detector 65 will also comprise a series of pulses, one pulse each time that the pin 63 rotates by the detector 65. The detector 65 is connected to an inverter I1 whose output is connected to the R input of the D flip-flop 69.

The Q output of the D flip-flop 69 will transpose to a logic one state on the rising edge of pulses produced by the detector 64 and transpose to a logic zero state on the falling edge of pulses produced by the detector 65. As a result, the signal at the Q output of the D flip-flop 69 will comprise a series of pulses such that each pulse has a duration, or duty cycle, dependent on the angular displacement of the pin 62 fixed to the disc 30 relative to the pin 63 fixed to the housing 22 secured to the rotating structure.

The series of varying duty cycle pulses is input to a low pass filter 70. The low pass filter produces an average duty cycle signal, that is, an average angular position signal by means of the integrating effect of a capacitor C3. The output of the low pass filter 70 is connected to an amplifier 71 which produces a position feedback signal comprising another input to the controller 68 as shown in FIG. 5.

The controller 68 in FIG. 5 is preferably an Xcite Master Controller manufactured by Zonic Technical Laboratories, Inc. of Cincinnati, Ohio. As pointed out above, both the torque feedback signal and the position feedback signal are input to the controller together with the preselected torque and position command signals from the respective torque and position setpoint circuits 59 and 72.

The controller 68 demodulates the torque command signal and generates a signal equal to the peak magnitude of the torque desired for exciting the structure to be tested. The controller 68 also demodulates the torque feedback signal and generates a signal equal to the peak magnitude of the actual torque applied to the rotating structure by the oscillating disc 30.

The controller 68 then generates a torque error signal dependent on the difference between the peak magnitude of the torque command signal and the peak magnitude of the torque feedback signal. The torque error signal is preferably integrated and then modulated onto a signal having the frequency preset by means of the torque setpoint circuit 59 in FIG. 5.

As mentioned earlier in conjunction with FIG. 2, the pins 62 and 63 are preferably located on the disc 30 and head 23 so that they are simultaneously sensed by the respective detectors 64 and 65 when the spacers 42 are at one end of the slots 33. When the spacers are in such a position in the slots, the duty cycle for pulses from the D flip-flop 69 in FIG. 6 is negligible, and, as a result, the average duty cycle signal is zero. On the other hand, if the pins 62 and 63 are sensed at different times the pulses from the D flip-flop 69 will have a non-zero duty cycle which causes the capacitor C3 to charge, and, as a result, the position feedback signal is dependent on the magnitude of the angular displacement of the disc 30 relative to the structure. The position feedback signal may vary over a range from zero to ten volts as the mean angular position of the spacers 42 in the slots 33 varies with respect to the ends of the slots 33.

The controller 68 in FIG. 5 inverts the position feedback signal and sums the resultant signal with the position command signal produced by the position setpoint circuit 72 in FIG. 5 to produce a position error signal. The controller then sums the position error signal with the modulated torque error signal to modify the modulated torque error signal and produce a composite error or control signal for energizing the servovalve 55.

The reason that the position error signal is preferably added to the modulated torque error signal is to assure that the control signal energizes the servovalve 55 so that pressurized fluid is supplied to the actuator 21 for oscillating the disc 30 symmetrically about the position in which the spacers 42 are centered in the slots 33. As a result, the disc 30 will oscillate relative to the structure in such a way that the spacers 42 do not bottom out on the ends of the slots 33 as the disc oscillates.

The control signal produced by the controller 68 energizes the servovalve 55 for controlling the supply of pressurized fluid from the hydraulic power supply 58 to the actuator 21. As a result, pressurized fluid is supplied to the chambers 46, 46', 46" and 47, 47', 47" so that the frequency and amplitude of differential pressure variations between the chambers in the actuator follow the variations in frequency and amplitude of the control signal. Consequently, the actuator oscillates the disc 30 with the desired frequency and amplitude set by the torque setpoint circuit 59. Furthermore, the actuator oscillates the disc symmetrically about the point set by the position setpoint circuit 72.

Finally, returning to the description of operation of the mechanical testing apparatus in FIG. 1, the actuator 21 oscillates the disc 30 as the actuator and disc rotate with the structure to be tested which is rotatably driven by energizing the motor 16. The oscillating disc 30 applies an oscillatory torque to the structure to be tested. The effects of the dynamic torsional force applied to the structure can be measured by any suitable means for determining such properties as the mechanical response characteristics, natural modes of vibration or fatigue life of the rotating structure.

The torsional exciter of the present invention is universal in application since it can be easily secured to any structure to be tested. The exciter can be easily adjusted to produce an oscillatory torque having a desired frequency and amplitude with a capability for applying a dynamic torsional force at a frequency as high as 1000 Hz. The exciter of the present invention is closed-loop so that the dynamic torsional force applied to the rotating structure is precisely controlled.

The exciter of the present invention includes many conventional, off-the-shelf components and is easy to construct. Consequently, the cost of production is relatively low.

A preferred embodiment of the torsional exciter of the present invention has been described above. Various modifications are contemplated, such as replacement of the pressure transducers by a torque cell and/or substitution of a rotary variable differential transformer for the position transducers. These and other modifications will be apparent to those of skill in the field and are considered to fall within the scope of the invention which can only be ascertained by reference to the appended claims.

We claim:

1. An exciter for applying torque to a rotating structure, comprising:
    a rotary hydraulic actuator including a first element and a second element, said second element being rotatable relative to said first element;
    means for securing one of said first and second elements to said rotating structure;
    an inertial mass mounted on the other of said first and second elements;
    a hydraulic power supply for supplying pressurized fluid; and
    electrohydraulic means for controlling said actuator, said electrohydraulic means including:
    (a) a torque setpoint circuit for selectively producing a torque command signal to set a desired amplitude and frequency for torque applied to said rotating structure;
    (b) means for producing a torque feedback signal dependent on the actual torque applied to said rotating structure;
    (c) a controller responsive to said command and feedback signals for producing a control signal; and
    (d) means interconnecting said hydraulic power supply and actuator and responsive to said control signal for controlling the supply of pressurized fluid to said actuator such that said actuator oscillates said inertial mass with respect to said rotating structure at said desired amplitude and frequency;
    whereby a controlled dynamic torsional force is applied to said rotating structure.

2. The exciter of claim 1 wherein said electrohydraulic means further includes:
    a position setpoint circuit for selectively producing a position command signal to set a desired midpoint of the arc through which said inertial mass oscillates; and
    means for producing a position feedback signal dependent on the average angular position of said inertial mass relative to said rotating structure as said inertial mass oscillates; and wherein said controller is responsive to said position command and position feedback signals for producing a position error signal and for modifying said control signal in response to said position error signal;
    whereby said inertial mass oscillates symmetrically about said desired midpoint.

3. The exciter of claim 2 wherein said torque setpoint circuit is adjustable for producing a random variation in the amplitude or frequency of the torque applied to said rotating structure.

4. The exciter of claim 2 wherein said first actuator element is a housing and said second actuator element is a driveshaft and wherein said inertial mass is a disc having arcuate slots, said disc being mounted on said driveshaft, said exciter further including a mounting plate secured to said housing for mounting said actuator on said rotating structure, said mounting plate being secured to said housing by mounting means including spacers extending through said slots and disposed between said housing and said disc, and wherein said means for producing a position feedback signal includes a first pin fixed to said housing and a second pin fixed to said disc, a first detector for sensing said first pin and a second detector for sensing said second pin and an interface circuit for producing an average position signal, said average position signal constituting said position feedback signal.

5. The exciter of claim 4 wherein said torque setpoint circuit is adjustable for producing a random variation in the amplitude or frequency of the torque applied to said rotating structure.

6. The exciter of claim 1 or 2 wherein said first actuator element is a housing and said second actuator element is a driveshaft and wherein said inertial mass is a disc mounted on said driveshaft, said exciter further including a mounting plate secured to said housing for mounting said housing on said rotating structure.

7. The exciter of claim 6 wherein said torque setpoint circuit is adjustable for producing a random variation in the amplitude or frequency of the torque applied to said rotating structure.

8. The exciter of claim 1 wherein said actuator further includes a first chamber and a second chamber and wherein said means for producing a torque feedback signal includes first and second pressure transducers and an interface circuit for producing a differential pressure signal dependent on the actual torque applied to said rotating structure, said differential pressure signal constituting said torque feedback signal.

9. The exciter of claim 8 wherein said torque setpoint circuit is adjustable for producing a random variation in the amplitude or frequency of the torque applied to said rotating structure.

10. The exciter of claim 1 wherein said torque setpoint circuit is adjustable for producing a random variation in the amplitude or frequency of the torque applied to said rotating structure.

11. An apparatus for mechanically testing a rotating structure to determine the response, natural modes of vibration or fatigue life of the rotating structure in the presence of dynamic torsional excitation, comprising:
   a rotary structure to be tested;
   a motor;
   a drivetrain interconnecting said rotary structure and motor;
   said motor being selectively energizable for activating said drivetrain to rotate said rotary structure;
   a rotary hydraulic actuator including a housing and a driveshaft, said driveshaft being rotatable relative to said housing;
   means for securing said housing to said rotating structure;
   an inertial mass mounted on said driveshaft;
   a hydraulic power supply for supplying pressurized fluid; and
   electrohydraulic means for controlling said actuator, said electrohydraulic means including:
   (a) a torque setpoint circuit for selectively producing a torque command signal to set a desired amplitude and frequency for torque applied to said rotating structure;
   (b) means for producing a torque feedback signal dependent on the actual torque applied to said rotating structure;
   (c) a controller responsive to said command and feedback signals for producing a control signal; and
   (d) means interconnecting said hydraulic power supply and actuator and responsive to said control signal for controlling the supply of pressurized fluid to said actuator such that said actuator oscillates said inertial mass with respect to said rotating structure at said desired amplitude and frequency;
   whereby a controlled dynamic torsional force is applied to said rotating structure.

12. The apparatus of claim 11 further including:
   a position setpoint circuit for selectively producing a position command signal to set a desired midpoint of the arc through which said inertial mass oscillates; and
   means for producing a position feedback signal dependent on the average angular position of said inertial mass relative to said rotating structure as said inertial mass oscillates; and wherein said controller is responsive to said position command and position feedback signals for producing a position error signal and for modifying said control signal in response to said position error signal;
   whereby said inertial mass oscillates symmetrically about said desired midpoint.

13. A method for applying torque to a rotating structure, including the steps of:
   securing one element of a rotary hydraulic actuator to the rotating structure;
   mounting an inertial mass on a second element of the actuator;
   providing a supply of pressurized fluid; and
   controlling the actuator for oscillating the second element with respect to the first element by
   (a) selectively producing a torque command signal to set a desired amplitude and frequency for torque applied to the rotating structure;
   (b) producing a torque feedback signal dependent on the actual torque applied to the rotating structure;
   (c) producing a control signal in response to the command and feedback signals, and
   (d) controlling the supply of pressurized fluid to the actuator in response to the control signal such that the actuator oscillates the inertial mass with respect to the rotating structure at the desired amplitude and frequency;
   thereby applying a controlled dynamic torsional force to the rotating structure.

14. The method of claim 13 further including the steps of:
   selectively producing a position command signal to set a desired midpoint of the arc through which the inertial mass oscillates;
   producing a position feedback signal dependent on the average angular position of the inertial mass with respect to the rotating structure as the inertial mass oscillates;
   producing a position error signal in response to the position command and position feedback signals; and
   modifying the control signal in response to the position error signal;
   thereby causing the inertial mass to oscillate symmetrically about the desired midpoint.

15. A method for mechanically testing a rotating structure to determine the response, natural modes of vibration or fatigue life of the rotating structure in the presence of dynamic torsional excitation, including the steps of:
   rotatably mounting a rotary structure;
   interconnecting the rotary structure to a motor by means of a drivetrain;
   securing the housing of a rotary hydraulic actuator having a driveshaft to the rotary structure;
   mounting an inertial mass on the driveshaft of the actuator;
   selectively energizing the motor for activating the drivetrain to rotate the rotary structure;
   providing a supply of pressurized fluid; and
   controlling the actuator for oscillating the driveshaft with respect to the housing by
   (a) selectively producing a torque command signal to set a desired amplitude and frequency for torque applied to the rotating structure;
   (b) producing a torque feedback signal dependent on the actual torque applied to the rotating structure;
   (c) producing a control signal in response to the command and feedback signals; and
   (d) controlling the supply of pressurized fluid to the actuator in response to the control signal such that the actuator oscillates the inertial mass with respect to the rotating structure at the desired amplitude and frequency;

thereby applying a controlled dynamic torsional force to the rotating structure.

16. The method of claim 15 further including the steps of:

selectively producing a position command signal to set a desired midpoint of the arc through which the inertial mass oscillates;

producing a position feedback signal dependent on the average angular position of the inertial mass relative to the rotating structure as the inertial mass oscillates;

producing a position error signal in response to the position command and position feedback signals; and modifying the control signal in response to the position error signal;

thereby causing the inertial mass to oscillate symmetrically about the desired midpoint.

17. torsional exciter for a rotating structure, comprising:

a rotary hydraulic actuator including a first element and a second element, said second element being rotatable relative to said first element;

means for securing one of said first and second elements to said rotating structure;

an inertial mass mounted on the other of said first and second elements;

a hydraulic power supply for supplying pressurized fluid; and electrohydraulic means for controlling said actuator, said electrohydraulic means including:

(a) means for selectively producing a position command signal correlated to a desired angular position of said inertial mass with respect to said rotating structure;

(b) means for producing a position feedback signal correlated to the actual angular position of said inertial mass with respect to said rotating structure;

(c) a controller responsive to said common and feedback signals for producing a control signal; and (d) means interconnecting said hydraulic power supply and actuator and responsive to said control signal for controlling the supply of pressurized fluid to said actuator such that said actuator angularly displaces said inertial mass with respect to said rotating structure;

whereby a torsional force is applied to said rotating structure.

18. The exciter of claim 17 wherein said electrohydraulic means further includes:

a torque setpoint circuit for selectively producing a torque command signal correlated to a desired torque applied to said rotating structure; and wherein said controller is responsive to said torque command signal for modifying said control signal in response to said torque command signal.

19. The exciter of claim 17 wherein said electrohydraulic means further includes:

a torque setpoint circuit for selectively producing a torque command signal correlated to a desired torque applied to said rotating structure; and means for producing a torque feedback signal dependent on the actual torque applied to said rotating structure; and wherein said controller is responsive to said torque command and torque feedback signals for modifying said control signal in response to said torque command and torque feedback signals;

whereby a controlled torsional force is applied to said rotating structure.

20. The exciter of claim 19 wherein said actuator further includes a first chamber and a second chamber and wherein said means for producing a torque feedback signal includes first and second pressure transducers and an interface circuit for producing a differential pressure signal dependent on the actual torque applied to said rotating structure, said differential pressure signal constituting said torque feedback signal.

21. The exciter of claim 18 or 19 wherein said torque setpoint circuit is adjustable for producing a random variation in the amplitude or frequency of the torque applied to said rotating structure.

22. The exciter of claim 17 wherein said first actuator element is a housing and said second actuator element is a driveshaft and wherein said inertial mass is a disc mounted on said driveshaft, said exciter further including a mounting plate secured to said housing for mounting said housing on said rotating structure.

23. The exciter of claim 17 wherein said first actuator element is a housing and said second actuator element is a driveshaft and wherein said inertial mass is a disc having arcuate slots, said disc being mounted on said driveshaft, said exciter further including a mounting plate secured to said housing for mounting said actuator on said rotating structure, said mounting plate being secured to said housing by mounting means including spacers extending through said slots and disposed between said housing and said disc, and wherein said means for producing a position feedback signal includes a first pin fixed to said housing and a second pin fixed to said disc, a first detector for sensing said first pin and a second detector for sensing said second pin and an interface circuit for producing an average position signal, said average position signal constituting said position feedback signal.

24. A method for torsionally exciting a rotating structure, including the steps of:

securing one element of a rotary hydraulic actuator to the rotating structure;

mounting an inertial mass on a second element of the actuator;

providing a supply of pressurized fluid; and controlling the actuator for angularly displacing the second element with respect to the first element by (a) selectively producing a position command signal correlated to a desired angular position of the inertial mass with respect to the rotating structure;

(b) producing a position feedback signal correlated to the actual angular position of the inertial mass with respect to the rotating structure;

(c) producing a control signal in response to the command and feedback signals; and (d) controlling the supply of pressurized fluid to the actuator in response to the control signal such that the actuator angularly displaces the inertial mass with respect to the rotating structure;

thereby applying a torsional force to the rotating structure.

25. The method of claim 24 further including the steps of:

selectively producing a torque command signal correlated to a desired torque applied to the rotating structure; and modifying the control signal in response to the torque command signal.

26. The method of claim 24 further including the steps of:

selectively producing a torque command signal correlated to a desired torque applied to the rotating structure;

producing a torque feedback signal correlated to the actual torque applied to the rotating structure; and modifying the control signal in response to the torque command and torque feedback signals;

thereby applying a controlled torsional force to said rotating structure.

* * * * *

UNITED STATES PATENT AND TRADEMARK OFFICE
CERTIFICATE OF CORRECTION

PATENT NO. : 4,283,957

DATED : August 18, 1981

INVENTOR(S) : Gerald J. Zobrist, Terry A. Dunlap, Richard H. Russell, and SeethaRamaiah Mannava It is certified that error appears in the above-identified patent and that said Letters Patent are hereby corrected as shown below:

On the title page SeethaRamaiah Mannava has been omitted as an inventor.

In the Inventors, "Gerald S. Zobrist" should be -- Gerald J --.

Column 2, line 24, "an" should be -- a --.

Column 3, line 25, "signals" should be -- signal --.

Column 5, line 27, "25'" second occurrence, should be -- 25'' --

Column 7, line 8, "24" should be -- 25 --.

Column 7, line 64, "R" should be -- $\bar{R}$ --.

Signed and Sealed this

Second Day of March 1982

[SEAL]

Attest:

GERALD J. MOSSINGHOFF

Attesting Officer

Commissioner of Patents and Trademarks